United States Patent
Spatafore et al.

(10) Patent No.: US 8,632,736 B2
(45) Date of Patent: Jan. 21, 2014

(54) FLOAT AND TUBE SYSTEM FOR SEPARATING A SUSPENSION WITH AN INTERNAL TRAP

(71) Applicant: RareCyte, Inc., Seattle, WA (US)

(72) Inventors: Paul Spatafore, Bothell, WA (US); Jackie Lynn Stilwell, Sammamish, WA (US); Arturo Ramirez, Seattle, WA (US); Evan Castiglia, Seattle, WA (US)

(73) Assignee: Rarecyte, Inc., Seattle, WA (US)

( * ) Notice: Subject to any disclaimer, the term of this patent is extended or adjusted under 35 U.S.C. 154(b) by 0 days.

(21) Appl. No.: 13/735,410

(22) Filed: Jan. 7, 2013

(65) Prior Publication Data

US 2013/0189168 A1    Jul. 25, 2013

Related U.S. Application Data

(60) Provisional application No. 61/583,866, filed on Jan. 6, 2012.

(51) Int. Cl.
```
B01D 45/00      (2006.01)
E04H 4/12       (2006.01)
B01D 33/00      (2006.01)
F16K 31/18      (2006.01)
B04B 1/00       (2006.01)
C12N 5/071      (2010.01)
G01N 1/18       (2006.01)
```

(52) U.S. Cl.
USPC ........... 422/533; 422/548; 210/121; 210/122; 210/222; 210/513; 137/409; 435/372; 436/177

(58) Field of Classification Search
None
See application file for complete search history.

(56) References Cited

U.S. PATENT DOCUMENTS

| | | | |
|---|---|---|---|
| 5,496,704 A | 3/1996 | Fiedler et al. | |
| 5,736,033 A * | 4/1998 | Coleman et al. | ............... 210/122 |
| 6,197,523 B1 | 3/2001 | Rimm et al. | |
| 6,444,436 B1 | 9/2002 | Rimm et al. | |
| 6,670,197 B2 | 12/2003 | Rimm et al. | |
| 6,911,315 B2 | 6/2005 | Rimm et al. | |
| 7,074,577 B2 | 7/2006 | Haubert et al. | |
| 7,129,056 B2 | 10/2006 | Rimm et al. | |
| 7,220,593 B2 | 5/2007 | Haubert et al. | |
| 7,329,534 B2 | 2/2008 | Haubert et al. | |
| 7,358,095 B2 | 4/2008 | Haubert et al. | |

(Continued)

FOREIGN PATENT DOCUMENTS

| WO | WO 011/126868 A1 | 10/2011 |
|---|---|---|
| WO | WO2011/126866 A1 | 10/2011 |
| WO | WO2011/126867 A1 | 10/2011 |

*Primary Examiner* — Jill Warden
*Assistant Examiner* — Julie Tavares

(57) ABSTRACT

This disclosure is directed to systems for separating a target analyte from a suspension. A suspension is added to a tube. A float is also added to the tube, and the tube, float, and suspension are centrifuged together, causing the constituent components of the suspension to separate into different layers along the axial length of the tube according to their specific gravities. The float has a specific gravity that positions the float at approximately the same level as a layer containing the target analyte, when the tube, float and sample are centrifuged. Prior to isolation, the material may be located between an outer surface of the float and an inner surface of the tube, or within a central bore that extends longitudinally through the float. The target analyte may then be drawn into a compartment within the float, thereby isolating the target analyte from the other suspension constituents.

20 Claims, 14 Drawing Sheets

(56) References Cited

U.S. PATENT DOCUMENTS

| | | |
|---|---|---|
| 7,495,827 B2 | 2/2009 | Grimes et al. |
| 7,560,277 B2 | 7/2009 | Weller, III |
| 7,629,176 B2 | 12/2009 | Haubert et al. |
| 7,915,029 B2 | 3/2011 | Haubert et al. |
| 7,919,049 B2 | 4/2011 | Haubert et al. |
| 8,012,742 B2 | 9/2011 | Haubert et al. |
| 2005/0186120 A1* | 8/2005 | Dorian et al. ............... 422/101 |
| 2010/0317106 A1 | 12/2010 | Levine et al. |
| 2011/0097816 A1* | 4/2011 | Goodwin ............... 436/178 |

\* cited by examiner

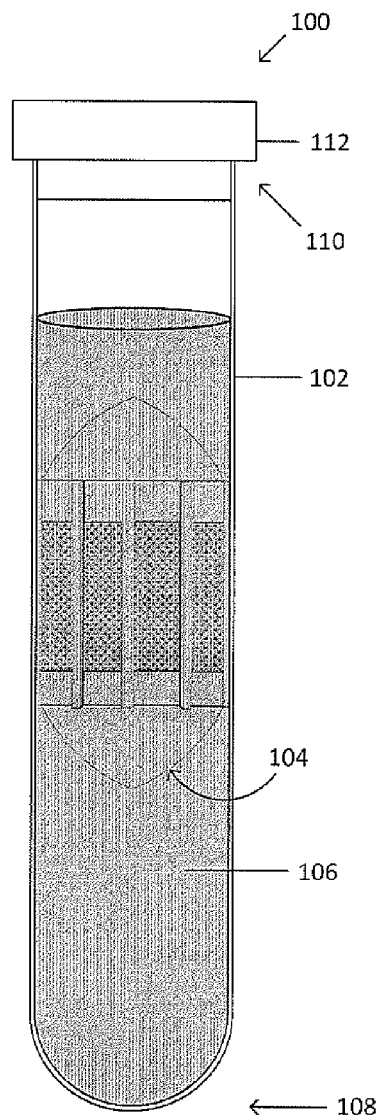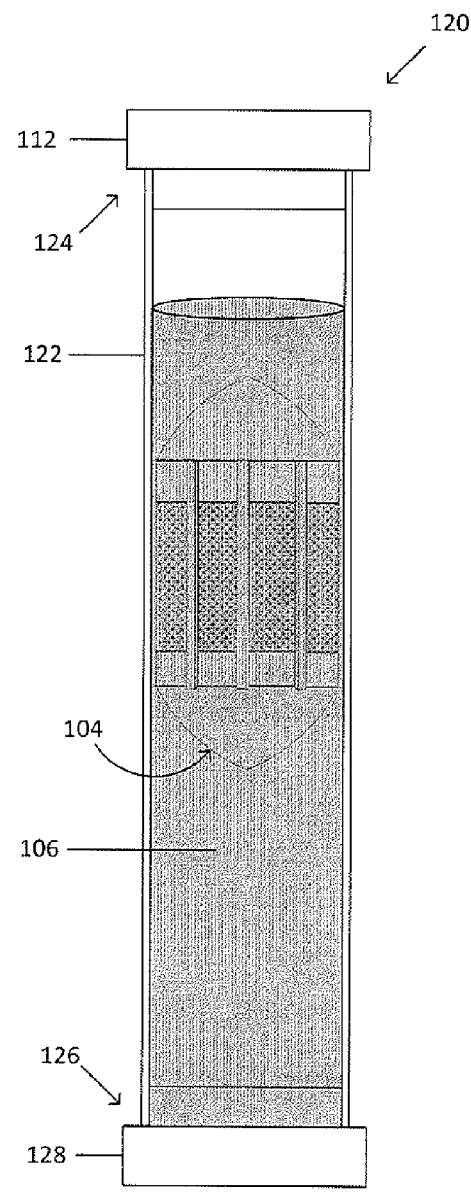
Fig. 1A
Fig. 1B

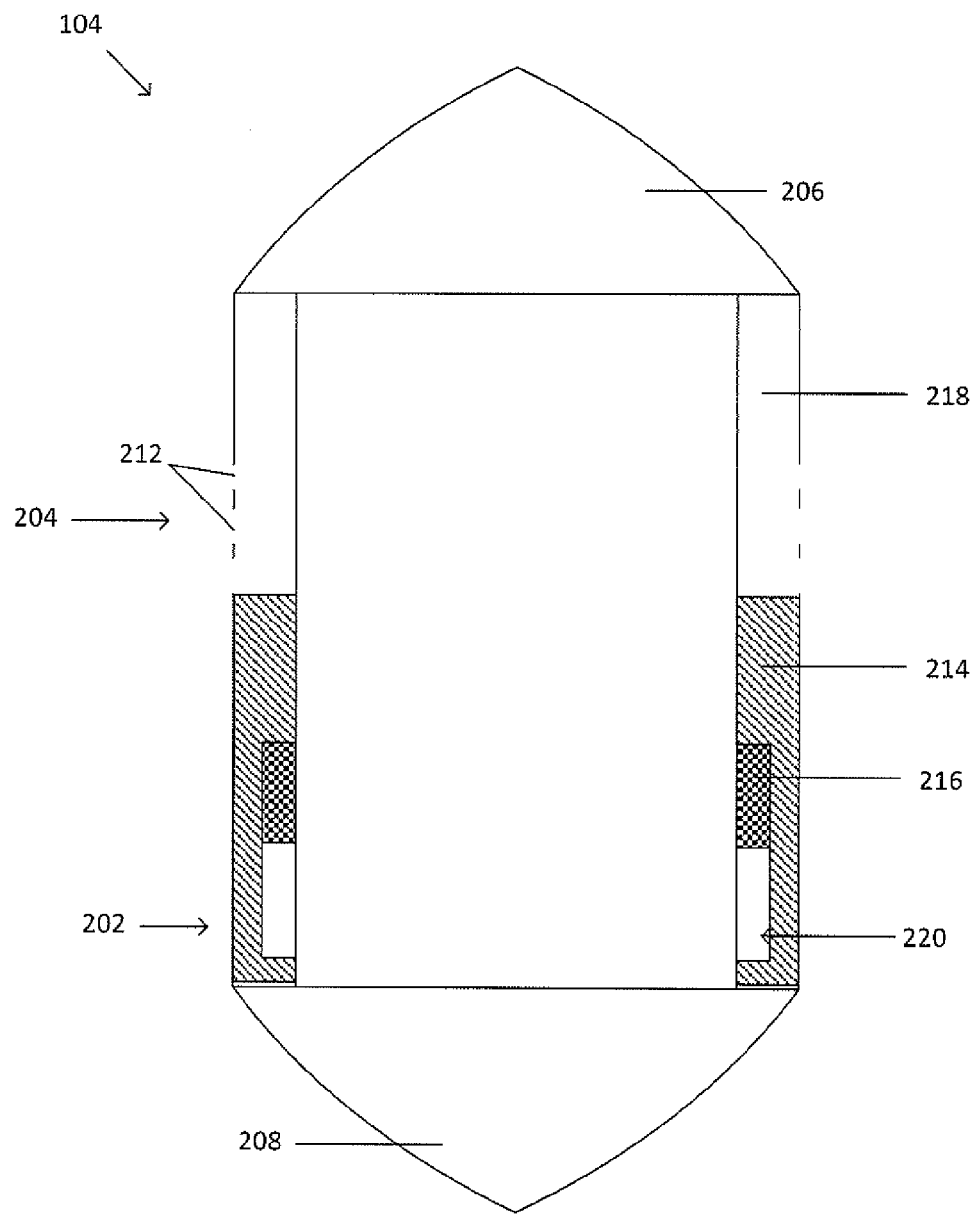

FLOAT AND TUBE SYSTEM FOR SEPARATING A SUSPENSION WITH AN INTERNAL TRAP

CROSS-REFERENCE TO A RELATED APPLICATION

This application claims the benefit of Provisional Application No. 61/583,866, filed Jan. 6, 2012.

TECHNICAL FIELD

This disclosure relates generally to density-based fluid separation and, in particular, to tube and float systems for the separation of constituent suspension components layered by centrifugation.

BACKGROUND

Suspensions often include materials of interest that are difficult to detect, extract and isolate for analysis. For instance, whole blood is a suspension of materials in a fluid. The materials include billions of red and white blood cells and platelets in a proteinaceous fluid called plasma. Whole blood is routinely examined for the presence of abnormal organisms or cells, such as fetal cells, endothelial cells, epithelial cells, parasites, bacteria, and inflammatory cells, and viruses, including HIV, cytomegalovirus, hepatitis C virus, and Epstein-Barr virus and nucleic acids. Currently, practitioners, researchers, and those working with blood samples try to separate, isolate, and extract certain components of a peripheral blood sample for examination. Typical techniques used to analyze a blood sample include the steps of smearing a film of blood on a slide 214 and staining the film in a way that enables certain components to be examined by bright field microscopy.

On the other hand, materials of interest composed of particles that occur in very low numbers are especially difficult if not impossible to detect and analyze using many existing techniques. Consider, for instance, circulating tumor cells ("CTCs"), which are cancer cells that have detached from a tumor, circulate in the bloodstream, and may be regarded as seeds for subsequent growth of additional tumors (i.e., metastasis) in different tissues. The ability to accurately detect and analyze CTCs is of particular interest to oncologists and cancer researchers, but CTCs occur in very low numbers in peripheral whole blood samples. For instance, a 7.5 ml sample of peripheral whole blood that contains as few as 3 CTCs is considered clinically relevant in the diagnosis and treatment of a cancer patient. However, detecting even 1 CTC in a 7.5 ml blood sample may be clinically relevant and is equivalent to detecting 1 CTC in a background of about 40-50 billion red and white blood cells. Using existing techniques to find, isolate and extract as few as 3 CTCs of a whole blood sample is extremely time consuming, costly and is extremely difficult to accomplish.

As a result, practitioners, researchers, and those working with suspensions continue to seek systems and methods to more efficiently and accurately detect, isolate and extract target materials of a suspension.

DESCRIPTION OF THE DRAWINGS

FIGS. 1A-1B show isometric views of two example tube and float systems.
FIGS. 2A-2C show an example of a float.

DETAILED DESCRIPTION

Figure 2A:
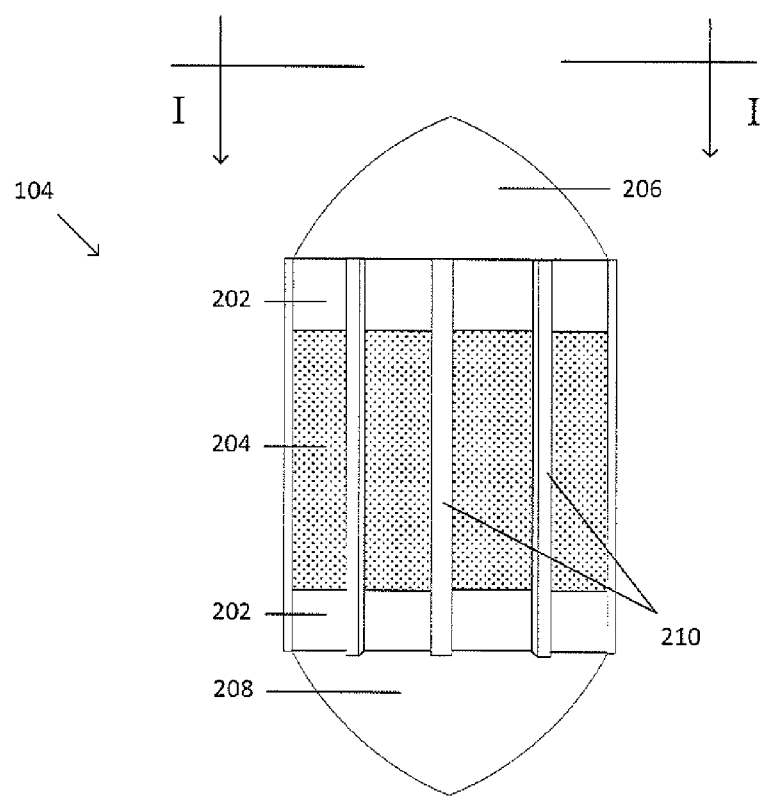

This disclosure is directed to systems for separating a target analyte from a suspension. A suspension is added to a tube. A float is also added to the tube, and the tube, float, and suspension are centrifuged together, causing the constituent components of the suspension to separate into different layers along the axial length of the tube according to their specific gravities. The float has a specific gravity that positions the float at approximately the same level as a layer containing the target analyte, when the tube, float and sample are centrifuged. Prior to isolation, the material may be located between an outer surface of the float and an inner surface of the tube, or within a central bore that extends longitudinally through the float. The target analyte may then be drawn into a compartment within the float, thereby isolating the target analyte from the other suspension constituents.

The detailed description is organized into two subsections: A general description of tube and float systems is provided in a first subsection. Methods for using tube and float systems are provided in a second subsection.

General Description of Tube and Float Systems

FIG. 1A shows an isometric view of an example tube and float system 100. The system 100 includes a tube 102 and a float 104 suspended within a suspension 106. In the example of FIG. 1A, the tube 102 has a circular cross-section, a first closed end 108, and a second open end 110. The open end 110 is sized to receive a stopper or cap 112. The tube may also have two open ends that are sized to receive stoppers or caps, such as the example tube and float system 120 shown FIG. 1B. The system 120 is similar to the system 100 except the tube 102 is replaced by a tube 122 that includes two open ends 124 and 126 configured to receive the cap 112 and a cap 128, respectively. The tubes 102 and 122 have a generally cylindrical geometry, but may also have a tapered geometry that widens, narrows, or a combination thereof toward the open ends 110 and 124, respectively. Although the tubes 102 and 122 have a circular cross-section, in other embodiments, the tubes 102 and 122 can have elliptical, square, triangular, rectangular, octagonal, or any other suitable cross-sectional shape that substantially extends the length of the tube. The tubes 102 and 122 can be composed of a transparent or semi-transparent flexible material, such as flexible plastic or another suitable material. The tube may also include a plug (not shown) at the closed end 108 to permit the removal of a fluid, the suspension, or a suspension fraction, whether with a syringe, a pump, by draining, or the like.

The tube may be rigid or flexible and the float may be rigid or flexible. When the tube 102 has a radially expandable sidewall with a natural first diameter, the float 104 can be captured within the tube 102 by an interference fit. In order to remove the float 104 from the tube 102 after the float 104 has been captured, or inserted into the tube 102, the expandable sidewall can be expanded radially to a larger diameter by applying an axial load, such as axial pressure due to centrifugation, an axial force produced by a clamp, external vacuum, or internally-introduced pressure. The larger diameter is sufficiently large to permit axial movement of the float 104 in the tube 102 during centrifugation. When a rigid tube and a rigid float are used together, neither will expand or constrict, thereby preventing any portion of the suspension, including the target analytes, from escaping between an outer surface of the float exterior and a wall of the tube. This forces the all portions of the suspension through the fluid passageway, wherein the target analytes will separate, by density, from the rest of the suspension and be trapped in the fluid compartment.

FIG. 2A shows an isometric view of the float 104 shown in FIG. 1. The float 104 includes a main body, including a solid portion 202 and a permeable portion 204, two teardrop-shaped end caps 206 and 208, and raised structural elements 210 radially spaced and axially oriented on the main body. The permeable portion 204 includes holes 212 to permit the passage of the target analyte from the separate suspension into float 104.

The float 104 can also include two dome-shaped end caps, two cone-shaped end caps, or the end caps can have any appropriate shape or geometry. The raised structural elements 210 extend outward from the main body to engage the inner wall of the tube 102. The solid portion 202 of the main body prevents fluids, materials, or the like from passing into or out of the float 104. The permeable portion 204 of the main body permits the passage of fluids, materials, or the like into and out of the float 104. The two teardrop-shaped caps 206 and 208 may be removable from the main body. The float 104 has a density substantially the same as the density of the target analyte.

Figure 2B:
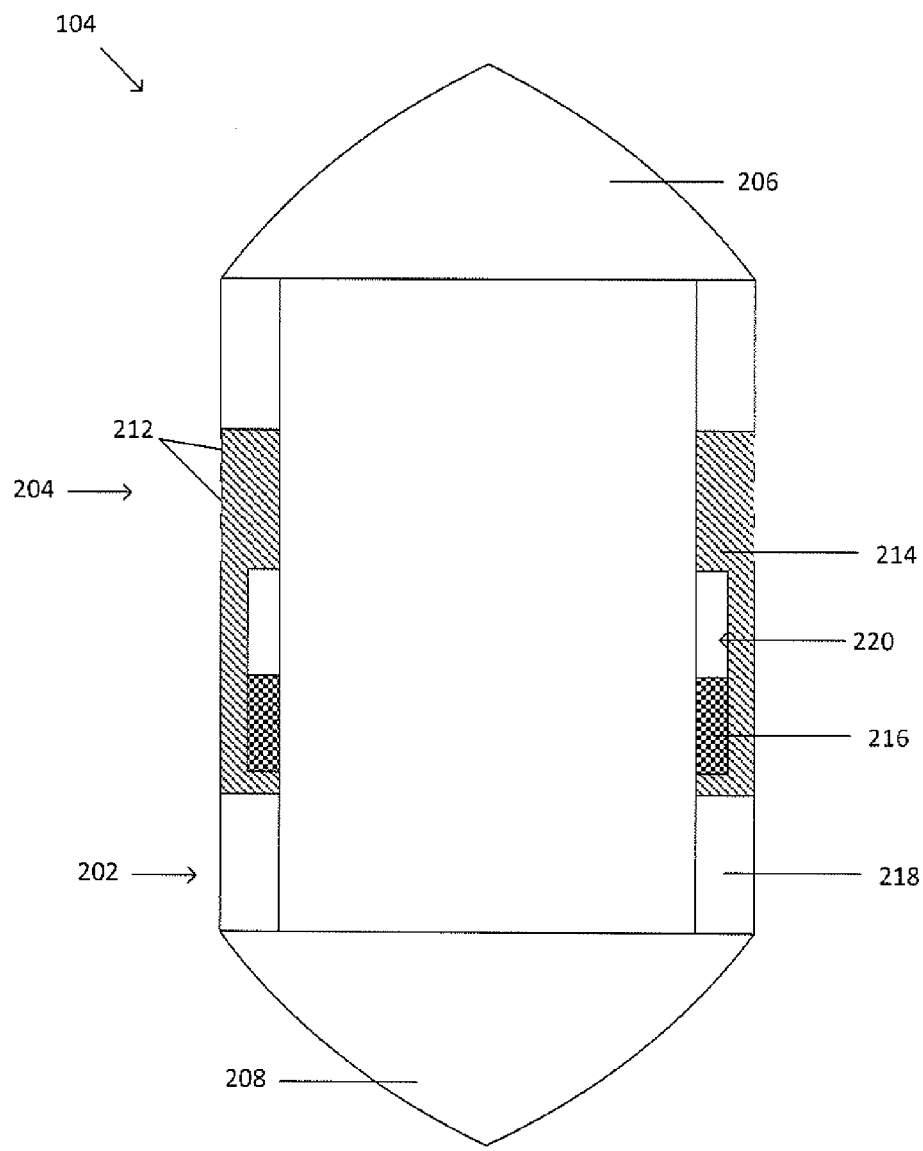

FIG. 2B shows a cross-section of the float 104 taken along a line I-I in which a slide 214, in a closed position, blocks passage of a target analyte through the permeable portion 204 of the main body. FIG. 2C shows a cross-section of the float 104 taken along the line I-I in which the slide 214, in an open position, permits the passage of a target analyte through the permeable portion 204 of the main body. As seen in FIGS. 2B and 2C, the main body further comprises a float compartment 218, the slide 214, and a catch 216. The permeable portion 204 of the main body is in fluid communication with the float compartment 218, so as to permit a target analyte to pass into the float compartment 218 through the permeable portion 204. The slide 214 is configured to block the passage of materials into the float compartment 218 when the slide 214 is in a closed position. The slide 214 includes a slide groove 220 to engage the catch 216 of the main body. The slide groove 220 engages the catch 216 of the main body to allow the slide 214 to slide within the main body while preventing the slide 214 from detaching or separating from the main body. The slide 214 has an outer diameter, an inner diameter, and a groove diameter. The groove diameter is less than or equal to the outer diameter; and the groove diameter is greater than the inner diameter.

The slide 214 may have a density greater than or less than the density of the main body of the float 104. By having different densities, the slide 214 may remain in a closed position during centrifugation and then may move into an open position after centrifugation. When the slide 214 is less dense than the main body, the permeable portion may be in a higher location on the main body, as the slide 214 may rise within the main body during centrifugation. Alternatively, when the slide 214 is denser than the main body, the permeable portion may be in a lower location on the main body, as the slide 214 may drop within the main body during centrifugation.

Figure 2D:
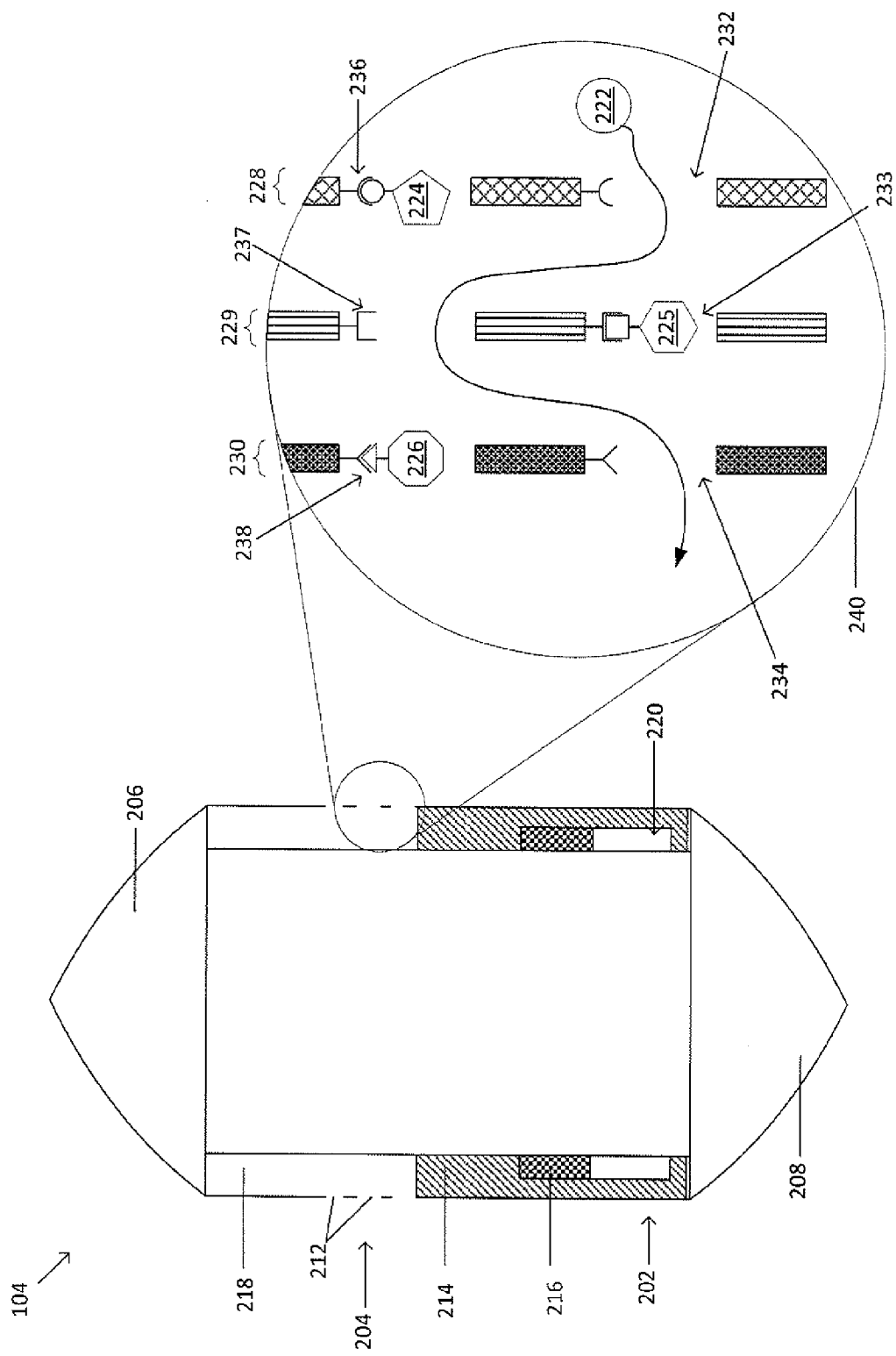
FIG. 2D-2F examples of floats.

FIG. 2D shows a cross-section of the float 104 taken along the line I-I with a permeable portion 204 that is selectively permeable. The permeable portion 204 of the main body may be selectively permeable. To be selectively permeable, the permeable portion 204 may comprise layers 228-230, as seen in magnified view 240, wherein each layer 228-230 includes holes 232-234 and the holes of each layer are bound with a specific type of attachment particle 236-238, such as an antibody. Each layer 228-230 may be configured to hold a non-target analyte 224-226, while permitting the passage of other analytes. This progressive selection permits a target analyte 222 to pass through all of the layers 228-230, while inhibiting contamination by preventing non-target analytes 224-226 from being collected within the float 104. For example, the permeable portion 204 may be fowled from three layers 228-230, each layer including holes that are sized to be larger than the target analyte 222. The outer layer 228 may be bound with antibodies to hold endothelial cells; the middle layer 229 may be bound with antibodies to hold epithelial cells; and the inner layer 230 may be bound with antibodies to hold mesenchymal cells. The target analyte 222, not being bound by any of the layers, passes through the layers 228-230 and into the float 104; whereas the epithelial, endothelial, and mesenchymal cells are held by the appropriate layer, thereby preventing those cells from passing into the float 104.

Figure 2E:
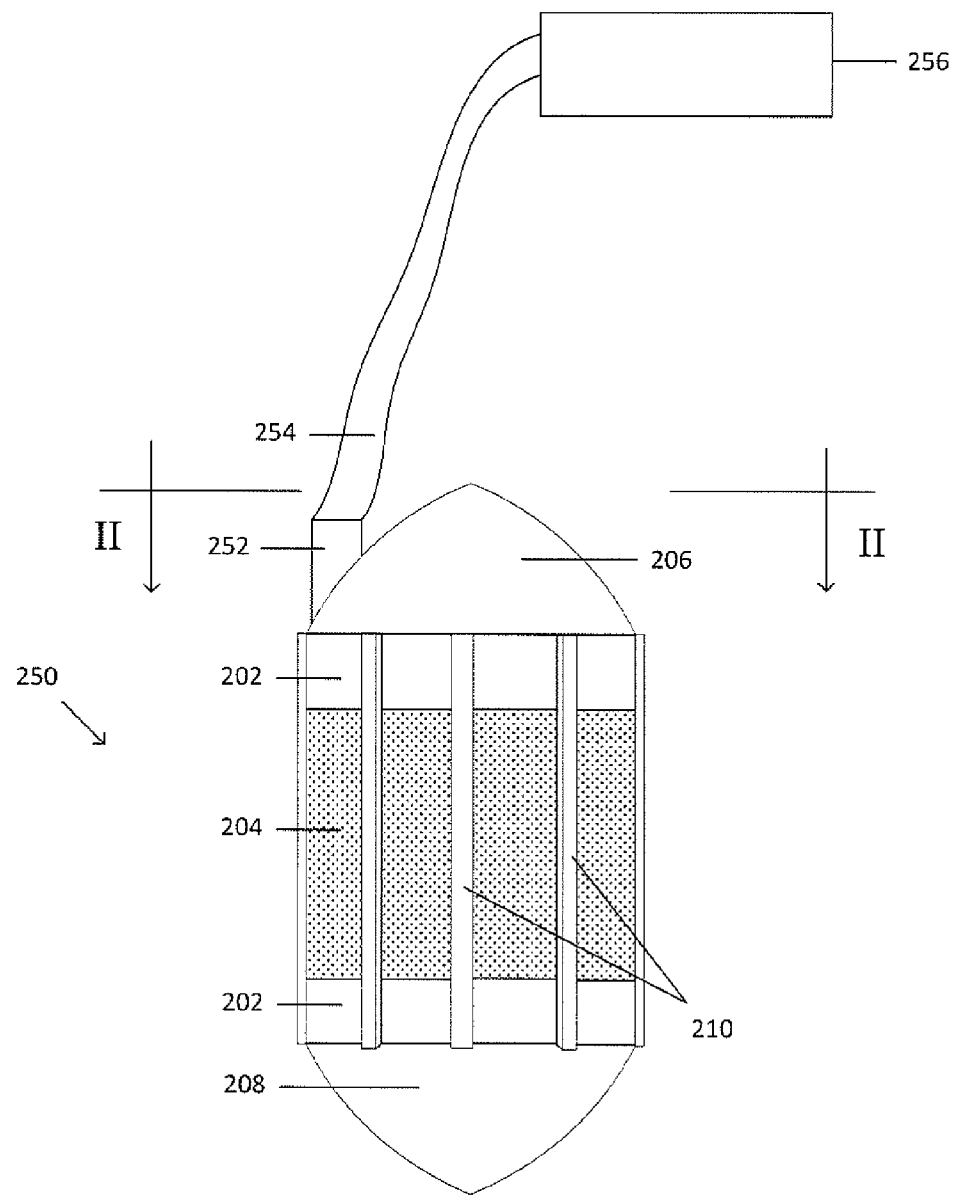
Figure 2F:
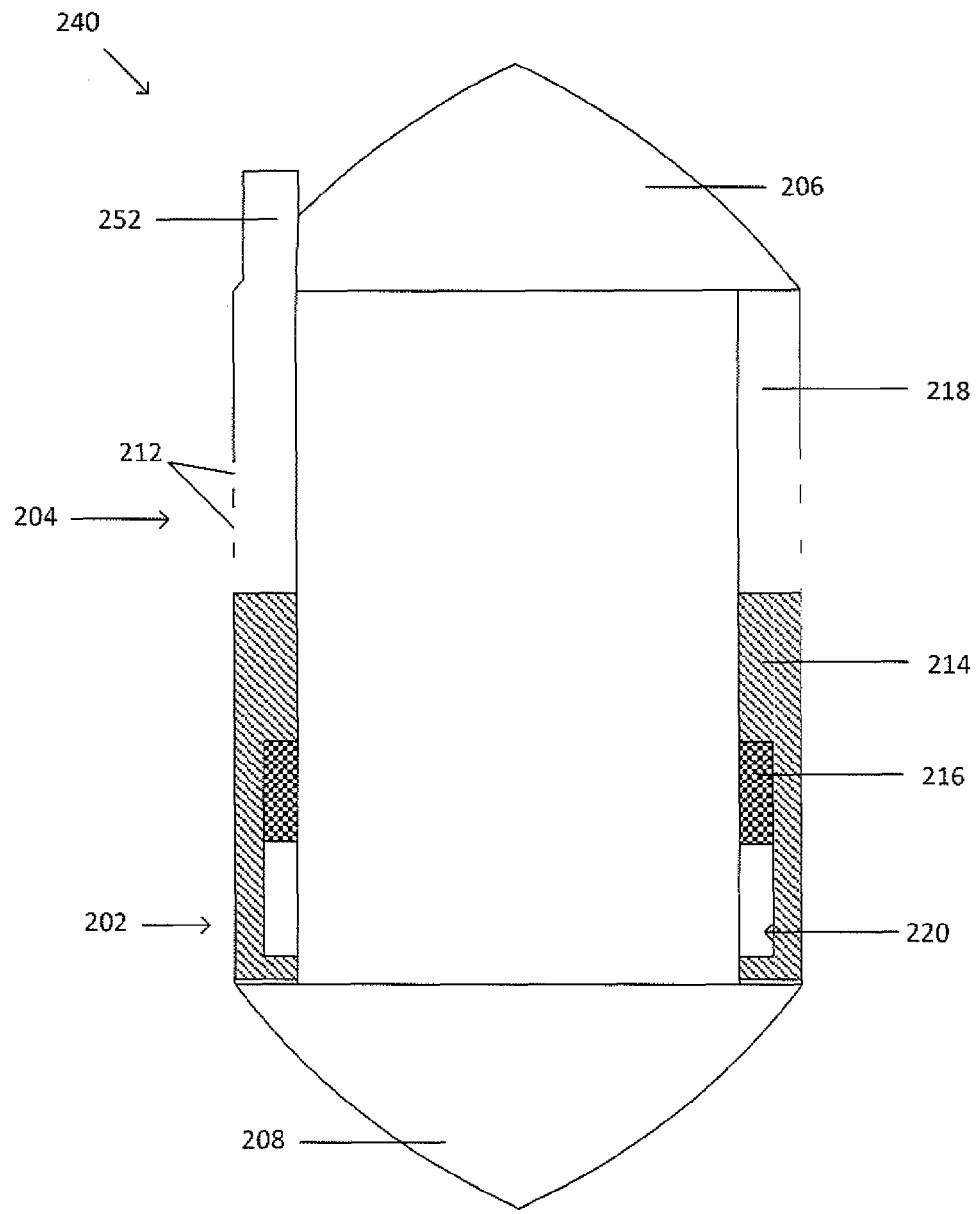

FIG. 2E shows a float 250 attached to a suction device 256 via a conduit 254. FIG. 2F shows a cross-section of the float 250 along a line II-II. The float 250 is similar to float 104, except that float 240 includes an adapter 252. The adapter 252 is in fluid communication with the float compartment 218, such that a pressure differential may be applied within the float compartment 218 after centrifugation by connecting the suction device 256 to the adapter 252 via the conduit 254. The suction device 256, such as a vacuum pump or a syringe, is configured to apply the pressure differential, such that a target analyte may be drawn into the float compartment 218.

In alternative embodiments, the number of raised structural elements, raised structural element spacing, and raised structural element thickness can each be independently varied. The raised structural elements 210 can also be broken or segmented. The main body is sized to have an outer diameter that is less than the inner diameter of the tube 102, thereby defining fluid retention channels between the outer surface of the main body and the inner wall of the tube 102. The surfaces of the main body between the raised structural elements 210 can be flat, curved or have another suitable geometry. In the example of FIG. 2A, the raised structural elements 210 and the main body 202 form a single structure.

Figure 3:
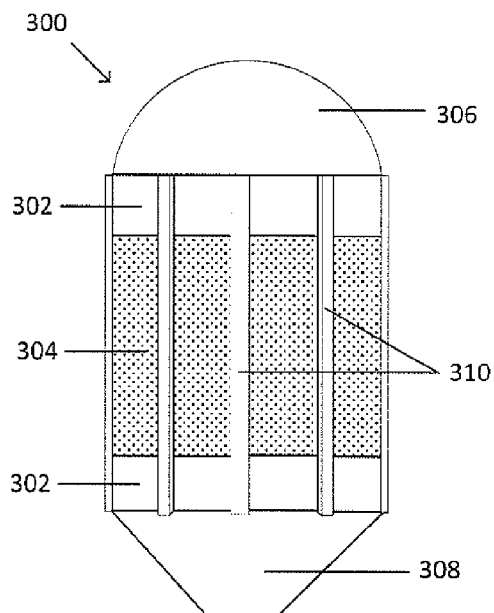
FIGS. 3-6 show examples of floats with different structural elements.

Embodiments include other types of geometric shapes for end caps. FIG. 3 shows an isometric view of an example float 300 with a dome-shaped end cap 306 and a cone-shaped end cap 308. A main body 306 of the float 300 can include the same solid portion 302 of the main body, the same permeable portion 304 of the main body, and the same raised structural elements 310 as the float 104. A float can also include a teardrop-shaped end cap. The float end caps can include other geometric shapes and are not intended to be limited to the shapes described herein.

Figure 4:
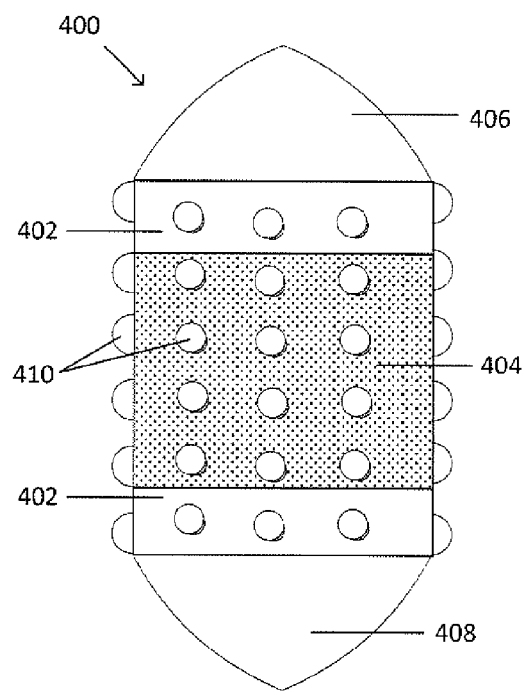
Figure 5:
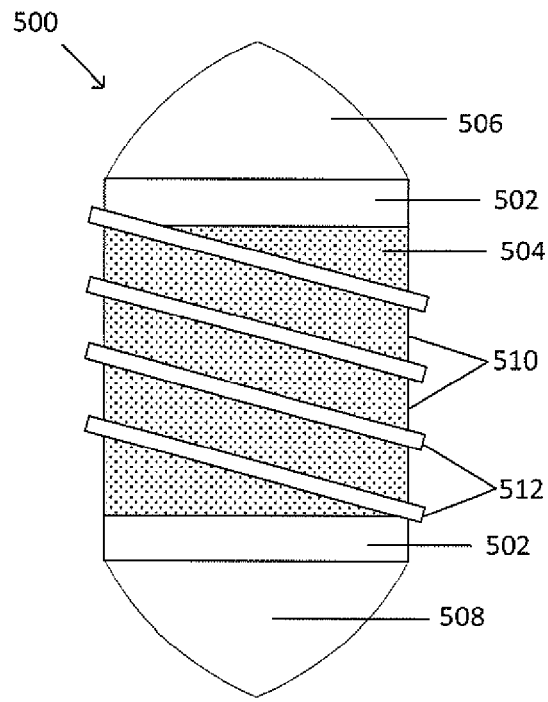
Figure 6:
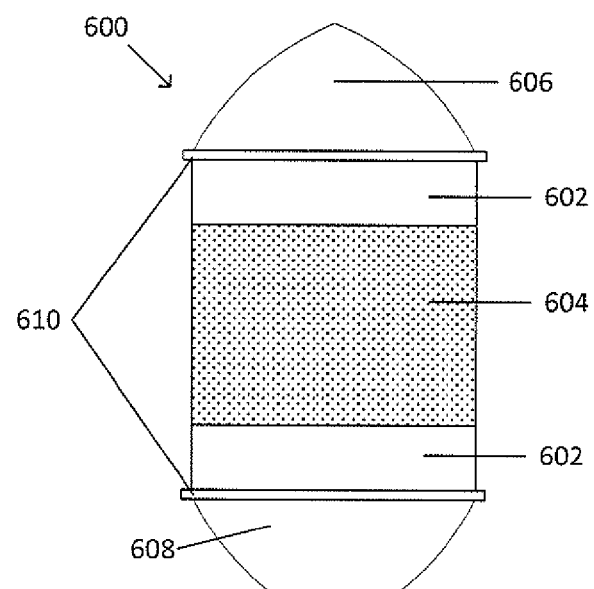

In other embodiments, the main body of the float 104 can include a variety of different raised structural elements for separating immunotherapeutic materials, supporting the tube wall, or directing the suspension fluid around the float during centrifugation. FIGS. 4, 5, and 6 show examples of different types of raised structural elements. Embodiments are not intended to be limited to these examples. In FIG. 4, a main body of a float 400 is similar to the float 104 except the main body includes a number of protrusions 410 that provide support for the tube. In alternative embodiments, the number and pattern of protrusions can be varied. In FIG. 5, a main body of a float 500 includes a single continuous helical structure or ridge 512 that spirals around the main body creating a helical channel 510. In other embodiments, the helical ridge 512 can be rounded or broken or segmented to allow fluid to flow between adjacent turns of the helical ridge 512. In various embodiments, the helical ridge spacing and rib thickness can be independently varied. In FIG. 6, a main body of a float 600 includes raised structural elements 610 extending circumferentially around the main body. One of the raised structural elements 610 can be omitted.

The float 600, including the circumferentially-extending raised structural elements 610, may also include alternative raised structural elements (not shown) on the main body. The alternative raised structural element (not shown) may be vertical, horizontal, or at least one helical ridge that spiral around the main body, or any appropriate raised structural element shape or configuration, as discussed above.

Figure 7A:
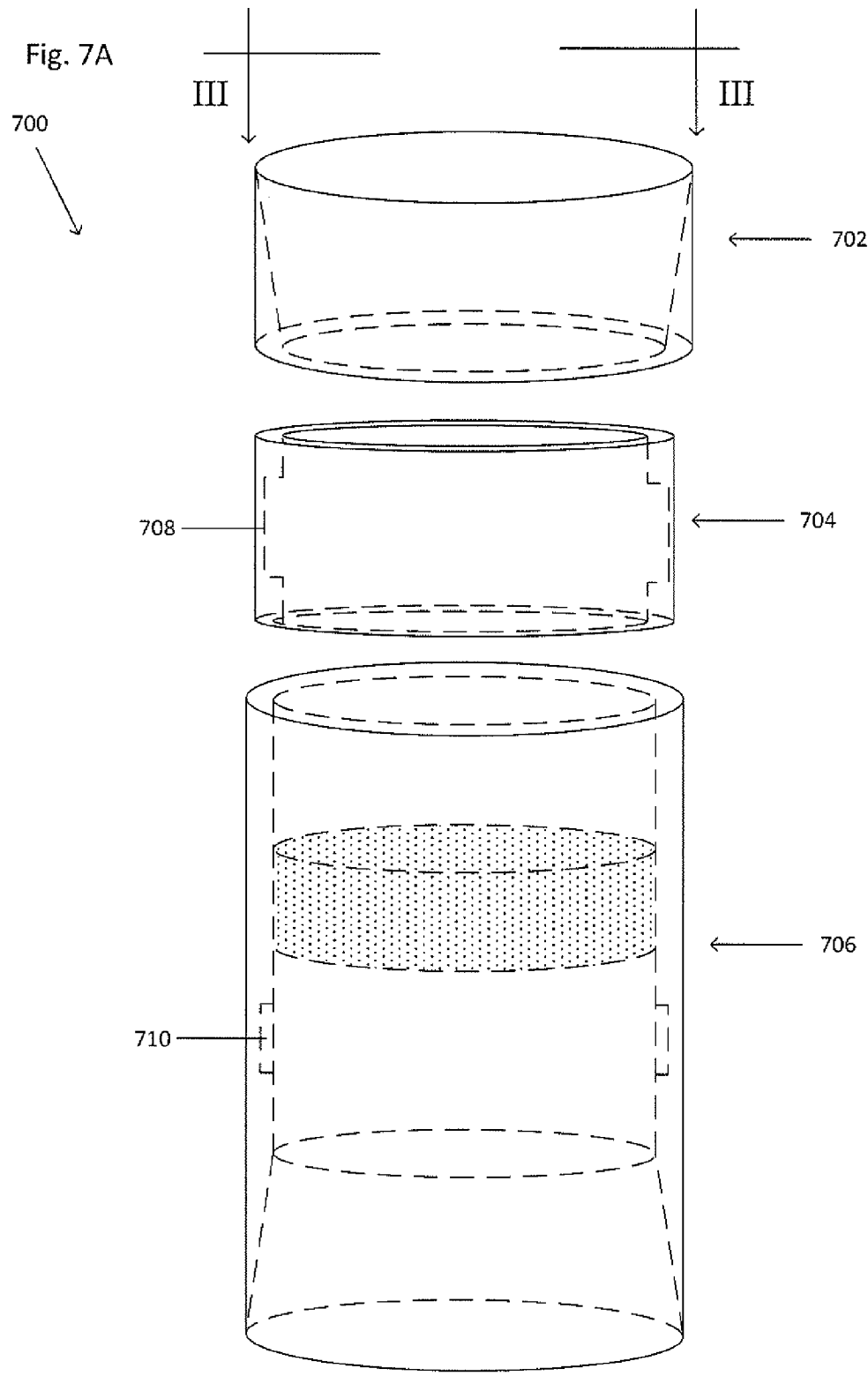
FIG. 7A-7C show an example of a float.
Figure 7B:
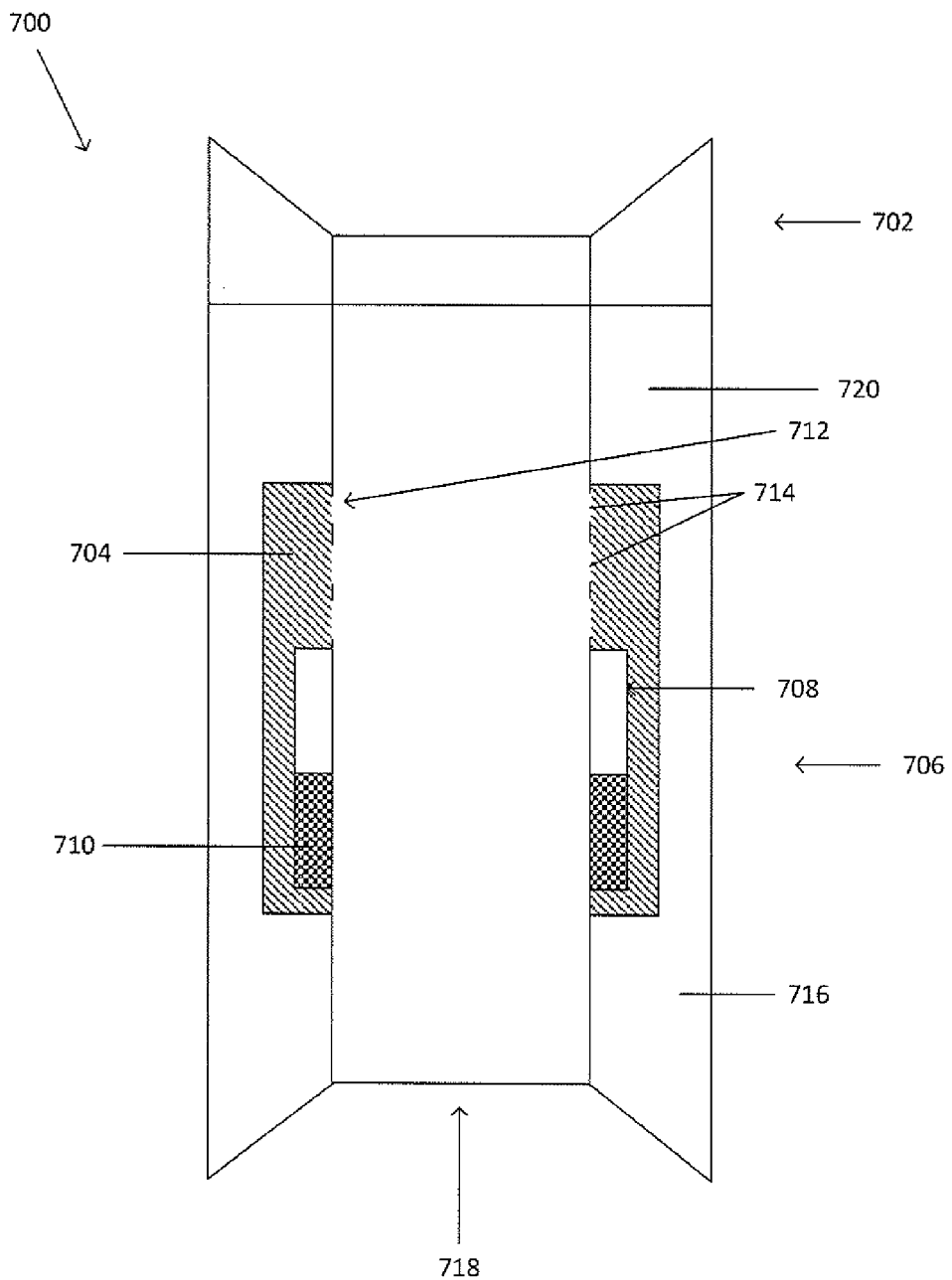
Figure 7C:
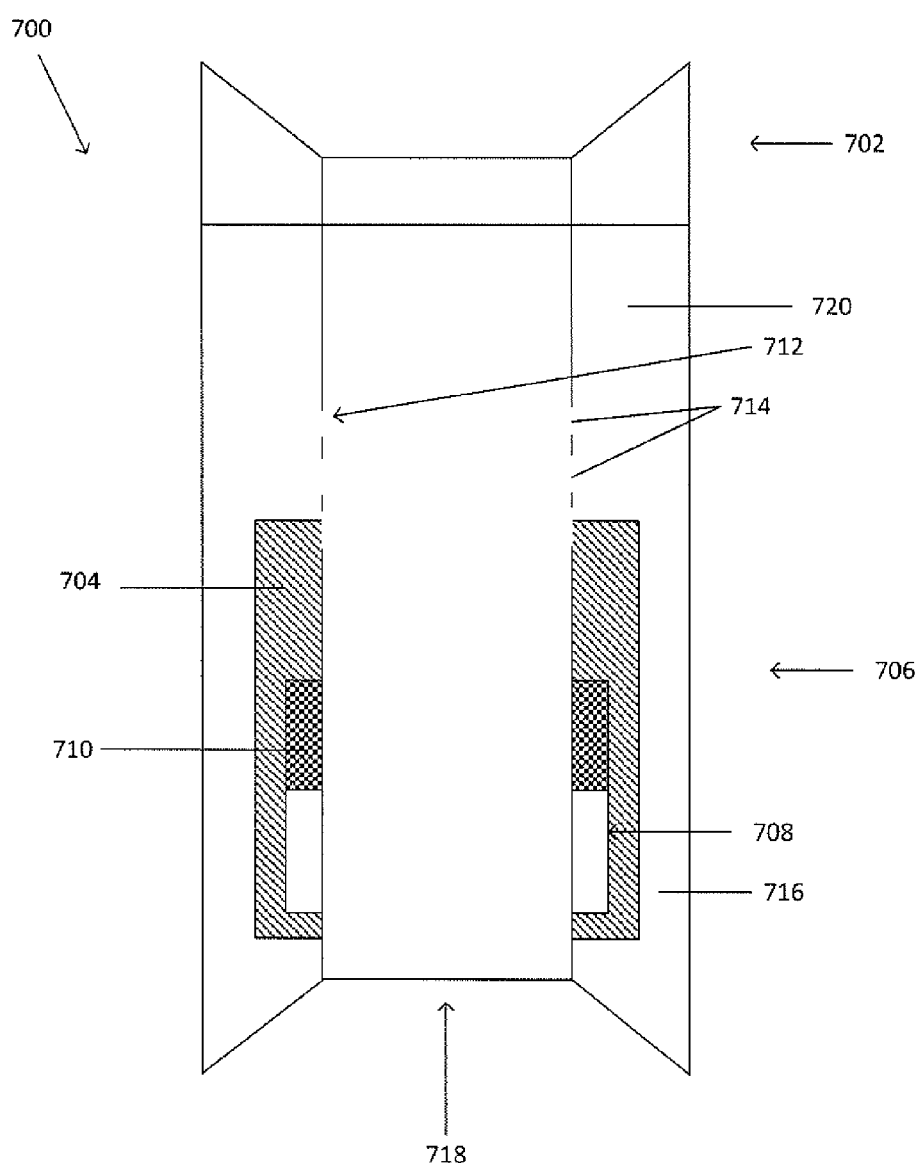

FIG. 7A shows an exploded view of a float 700. FIG. 7B shows a cross-section of the float 700 taken along a line in which a slide 704, in a closed position, blocks passage of a target analyte through the permeable portion 712 of the main body. FIG. 7C shows a cross-section of the float 700 taken along the line in which the slide 704, in an open position, permits the passage of a target analyte through the permeable portion 712 of the main body. The float 700 is similar to float 104, except that float 700 may not include support members, and the suspension and the suspension components are forced into a fluid passageway 720, the fluid passageway 720 being a bore that extends longitudinally through a cap 702 and the main body 706. The fluid passageway 720 includes a permeable portion 712, which includes holes 714. The main body 706 may include a bottom end having a concavity to force the suspension and suspension components into the fluid passageway 720 during and/or after centrifugation. The concavity may be conical or hemispherical. The float 700 may also include the cap 702 having a concavity to force the suspension and suspension components into the fluid passageway 720 during and/or after centrifugation. The concavity may be conical or hemispherical. The slide 704 includes a slide groove 708.

The float can be composed of a variety of different materials. The float can be composed of a metal, including, but not limited to, aluminum, brass, gold, silver, tin, copper, bronze, chromium, cobalt, nickel, lead, iron, steel, manganese, zinc, neodymium, and combinations thereof. The float can be composed of a organic or inorganic materials; ferrous plastics; sintered metal; machined metal; and plastic materials, such as polyoxymethylene ("Delrin®"), polystyrene, acrylonitrile butadiene styrene ("ABS") copolymers, aromatic polycarbonates, aromatic polyesters, carboxymethylcellulose, ethyl cellulose, ethylene vinyl acetate copolymers, nylon, polyacetals, polyacetates, polyacrylonitrile and other nitrile resins, polyacrylonitrile-vinyl chloride copolymer, polyamides, aromatic polyamides ("aramids"), polyamide-imide, polyarylates, polyarylene oxides, polyarylene sulfides, polyarylsulfones, polybenzimidazole, polybutylene terephthalate, polycarbonates, polyester, polyester imides, polyether sulfones, polyetherimides, polyetherketones, polyetheretherketones, polyethylene terephthalate, polyimides, polymethacrylate, polyolefins (e.g., polyethylene, polypropylene), polyallomers, polyoxadiazole, polyparaxylene, polyphenylene oxides (PPO), modified PPOs, polystyrene, polysulfone, fluorine containing polymer such as polytetrafluoroethylene, polyurethane, polyvinyl acetate, polyvinyl alcohol, polyvinyl halides such as polyvinyl chloride, polyvinyl chloride-vinyl acetate copolymer, polyvinyl pyrrolidone, polyvinylidene chloride, specialty polymers, polystyrene, polycarbonate, polypropylene, acrylonitrite butadiene-styrene copolymer, butyl rubber, ethylene propylene diene monomer, others, and combinations thereof.

Methods for Using Tube and Float Systems

Methods for isolating a target analyte from other suspension constituents are now described. The methods, in practice, can be used with any kind of suspension. For example, a sample suspension can be urine, blood, bone marrow, cystic fluid, ascites fluid, stool, semen, cerebrospinal fluid, nipple aspirate fluid, saliva, amniotic fluid, vaginal secretions, mucus membrane secretions, aqueous humor, vitreous humor, vomit, and any other physiological fluid or semi-solid. It should also be understood that a disease-carrying analyte can be a cell, such as ova or a circulating tumor cell ("CTC"), a circulating endothelial cell, a vesicle, a liposome, a protein, a nucleic acid, a biological molecule, a naturally occurring or artificially prepared microscopic unit having an enclosed membrane, parasites, microorganisms, viruses, or inflammatory cells.

A suspension is transferred to the tube of a tube and float system, such as the tube and float systems 100 and 120 shown in FIG. 1. A float is added to the tube and the cap is attached to seal the open end of the tube. The tube, float, and suspension are centrifuged for a period of time sufficient to allow separation of particles suspended in the suspension according to their specific gravities. The float has been selected with a density that positions the float 104 at approximately the same level as the target analyte within the tube.

The slide 214 is then moved from a closed position to an open position, thereby exposing the holes of the permeable portion 204, to permit passage of the target analyte into the float compartment. To cause the target analyte to pass through the permeable portion of the main body and into the float compartment, pressure gradient, such as by a vacuum, may be applied, such that the target analyte is pulled, sucked, pushed, or the like into the float compartment. The vacuum may be created within the float compartment 218 of the main body prior to centrifugation. The slide, prior to and during centrifugation, remains in a closed position due an outside force or mechanism or due to the density of the slide 214 being equal to or greater than the main body. During centrifugation, the target analyte will settle in the fluid passageway of the main body, as it will have a density equal to that of the float. After centrifugation, however, the slide 214 may be moved into the open position. The slide 214 may be moved from the closed position to the open position using an outside force or mechanism. The outside force or mechanism may include a magnet embedded in the slide 214 and then using a separate magnet to move the slide 214 to the open position; the slide 214 may further comprise a shaft extending through a portion of the teardrop-shaped cap which an operator may grab and pull to move the slide 214 into the open position; there may be a release which holds the slide 214 down (the slide 214 being held down by a separate force such as that caused by a spring, the release itself, or pressure) and then will be removed, thereby causing the slide 214 to move into the open position; or gravity may cause the slide 214 to move, due to the difference in densities between the slide 214 and the main body. The release may be on the outside of the main body such that contact by the release with the tube will cause the slide 214 to move into the open position; the release may be located anywhere on the float so that the slide 214 may be released and moved into the open position.

Alternatively, to draw the target analyte into the float 104 via a pressure differential, suction, or the like, one of the caps 206 and 208 may include an adapter (not shown) that is in fluid communication with the float compartment 218. After undergoing density-based separation by centrifugation, a conduit, such as a hose or tubing, may be connected to the adapter (not shown). The hose or tubing is then connected to a pump, syringe, or the like, to cause a pressure differential, suction, or the like within the float compartment 218, thereby drawing the target analyte 804 into the float compartment 218.

Figure 8A:
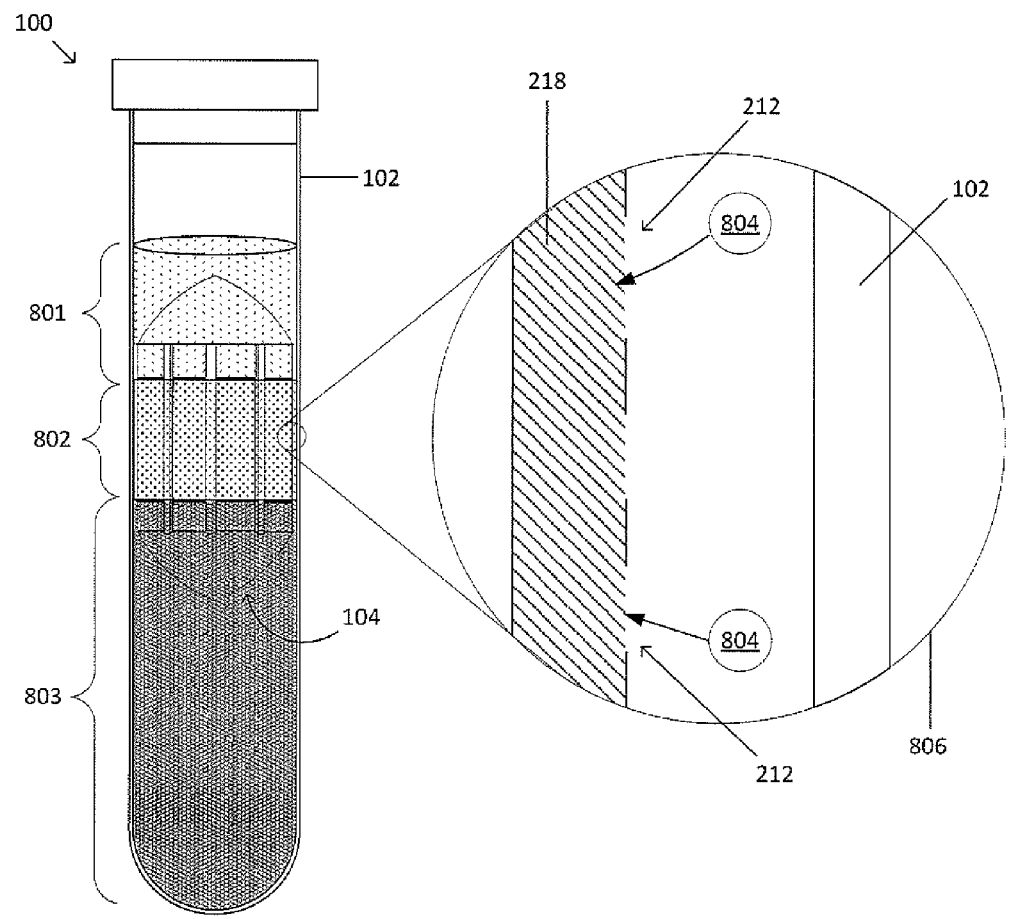
FIG. 8A shows an example float used to trap a target analyte.

For example, FIG. 8A shows a first example suspension composed of a sample of anticoagulated whole blood combined with the sample separated into a plasma layer 801, a Buffy coat layer 802, and a red blood cell layer 803. The float 104 spreads the Buffy coat 802 between the main body of the float 104 and inner wall of the tube 102 with red blood cells 803 packed below the Buffy coat 802 and the plasma 801 located above the Buffy coat 802. A slide (not shown) is moved from a closed position, thereby preventing materials from entering a float compartment 218, to an open position, thereby making the float compartment 218 accessible to a target analyte 804 via holes 212. The magnified view 806 depicts the target analyte 804 being drawn into the float compartment 218 through holes 212 of a permeable portion 204 of the main body.

Figure 8B:
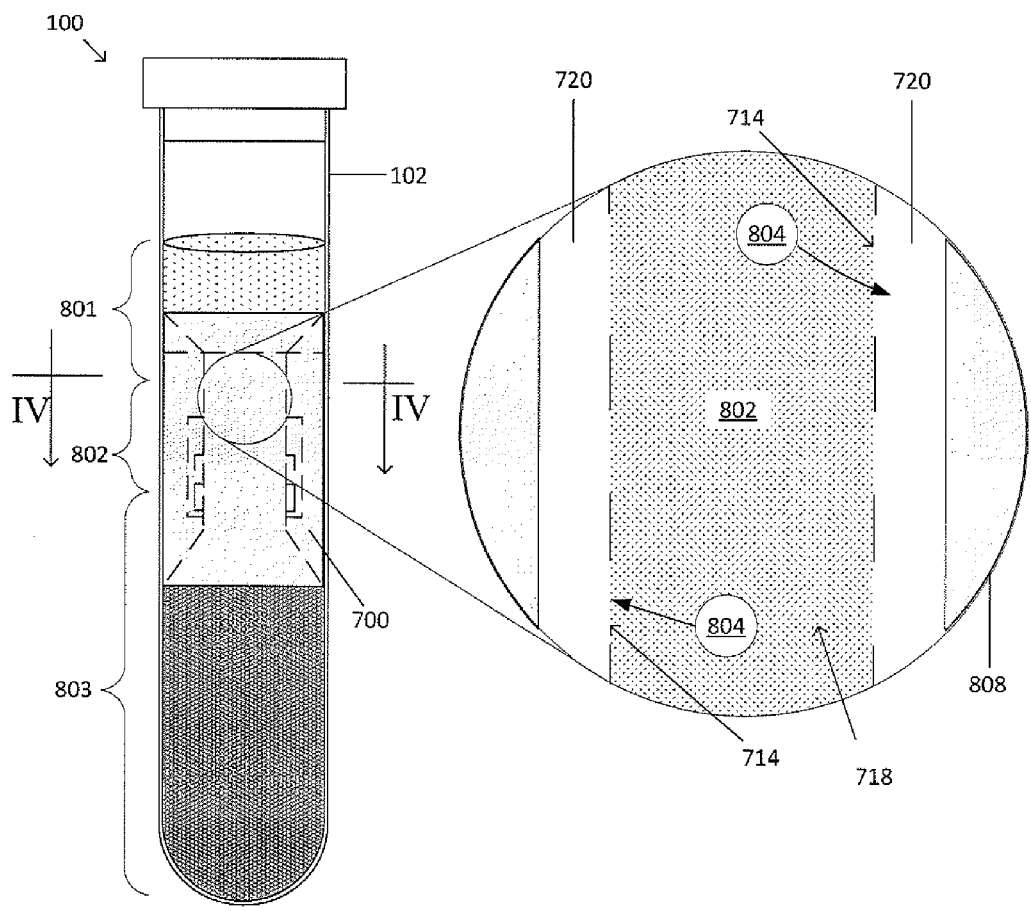
FIG. 8B shows an example float used to trap a target analyte.

Alternatively, FIG. 8B shows the first example suspension composed of a sample of anticoagulated whole blood combined with the sample separated into the plasma layer 801, the Buffy coat layer 802, and the red blood cell layer 803. A float 700 forces the Buffy coat 802 into a fluid passageway 718 with red blood cells 803 packed below the Buffy coat 802 and the plasma 801 located above the Buffy coat 802. A slide (not shown) is moved from a closed position, thereby preventing materials from entering a float compartment 720, to an open position, thereby making the float compartment 720 accessible to the target analyte 804 via holes 714. The magnified view 808 is a cross-section of the system taken along a line IV-IV. The magnified view 808 depicts the target analyte 804 being drawn into the float compartment 720 through holes 714 of a permeable portion 712 of the main body.

After the target analyte has passed into the float compartment, the float may be removed from the tube. After the float has been removed from the tube, one of the caps 206 and 208 may then be removed from the main body, such that the target analyte is now accessible. The target analyte may then be analyzed using any appropriate analysis method or technique, though more specifically intracellular analysis including intracellular or extracellular protein labeling; nucleic acid analysis, including, but not limited to, nucleic acid microarrays; protein microarrays; fluorescent in situ hybridization ("FISH"—a tool for analyzing DNA and/or RNA, such as gene copy number changes); or branched DNA ("bDNA"—a tool for analyzing DNA and/or RNA, such as mRNA expression levels) analysis. These techniques use fixation, permeabilization, and isolation of the target analyte prior to analysis. Some of the intracellular proteins which may be labeled include, but are not limited to, cytokeratin ("CK"), actin, Arp2/3, coronin, dystrophin, FtsZ, myosin, spectrin, tubulin, collagen, cathepsin D, ALDH, PBGD, Akt1, Akt2, c-myc, caspases, survivin, $p27^{kip}$, FOXC2, BRAF, Phospho-Akt1 and 2, Phospho-Erk1/2, Erk1/2, P38 MAPK, Vimentin, ER, PgR, PI3K, pFAK, KRAS, ALKH1, Twist1, Snail1, ZEB1, Slug, Ki-67, M30, MAGEA3, phosphorylated receptor kinases, modified histones, chromatin-associated proteins, and MAGE. To fix, permeabilize, or label, fixing agents (such as formaldehyde, formalin, methanol, acetone, paraformaldehyde, or glutaraldehyde), detergents (such as saponin, polyoxyethylene, digitonin, octyl β-glucoside, octyl β-thioglucoside, 1-S-octyl-β-D-thioglucopyranoside, polysorbate-20, CHAPS, CHAPSO, (1,1,3,3-Tetramethylbutyl)phenyl-polyethylene glycol or octylphenol ethylene oxide), or labeling agents (such as fluorescently-labeled antibodies, Pap stain, Giemsa stain, or hematoxylin and eosin stain) may be used.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

We claim:

1. A float for use in a float and tube system for separating a suspension suspected of containing a target analyte, the float comprising:
   a main body including a float compartment and a permeable portion with at least one hole to permit passage of the target analyte into the float compartment; and,
   a slide located within the float compartment to block the at least one hole and prevent passage of the target analyte into the float compartment when the slide is in a closed position.

2. The float of claim 1, the float compartment to hold the target analyte upon passage of the target analyte through the permeable portion.

3. The float of claim 1, the main body further comprising a catch to prevent the slide from detaching or separating from the main body.

4. The float of claim 3, the slide further comprising a groove to engage the catch.

5. The float of claim 4, the slide having a density that is less than a density of the main body.

6. The float of claim 4, the slide having a density that is greater than a density of the main body.

7. The float of claim 1, the at least one hole being exposed to permit passage of the target analyte into the float compartment when the slide is moved into an open position.

8. The float of claim 1, the permeable portion further comprising a plurality of layers, wherein each layer includes at least one hole and the at least one hole of each layer is bound with an attachment particle to bind non-target analytes, and wherein no two layers have the same type of attachment particle.

9. The float of claim 1, the float compartment further comprising a vacuum to draw the target analyte into the float compartment when the slide is in an open position.

10. The float of claim 1, the slide further comprising an embedded magnet.

11. The float of claim 1, further comprising a cap to cover the float compartment, and the slide further comprising a shaft to extend through the cap.

12. The float of claim 1, the main body further comprising a release to hold the slide in a closed position when active and to permit the slide to move into an open position when not active.

13. The float of claim 1, wherein the permeable portion is on an outer surface of the main body.

14. The float of claim 1, further comprising a cap to cover the float compartment, a fluid passageway extending longitudinally through the cap and the main body, wherein the fluid passageway further comprises the permeable portion of the main body to permit passage of the target analyte into the float compartment when the slide is in an open position.

15. The float of claim 14, wherein the cap has a conical or hemi-spherical concavity.

16. The float of claim 15, the main body further comprising a bottom end, wherein the bottom end is a conical or hemi-spherical concavity.

17. The float of claim 1, further comprising: a cap to cover the float compartment, an adapter extending from the cap, the adapter to connect to a suction device via a conduit, and the adapter being in fluid communication with the float compartment to provide a pressure differential upon activation of the suction device.

18. A system for separating a suspension suspected of containing a target analyte, the system comprising:
a float, comprising:
a main body including a float compartment and a permeable portion with at least one hole to permit passage of the target analyte into the float compartment,
a slide located within the float compartment to block the at least one hole and prevent passage of the target analyte into the float compartment when the slide is in a closed position,
a cap to cover the float compartment,
an adapter to extend from the cap,
a conduit; and
a suction device, the conduit to connect the adapter to the suction device, and the adapter being in fluid communication with the float compartment to provide a pressure differential upon activation of the suction device.

19. The system of claim 18, wherein the suction device is a vacuum pump or a syringe.

20. A system for separating a suspension suspected on containing a target analyte, the system comprising:
a float comprising:
a main body including a float compartment and a permeable portion with at least one hole to permit passage of the target analyte into the float compartment, and
a slide located within the float compartment to block the at least one hole and prevent passage of the target analyte into the float compartment when the slide is in a closed position;
and
a tube to hold the suspension and the float.

* * * * *